United States Patent [19]
Chance

[11] Patent Number: 5,081,991
[45] Date of Patent: Jan. 21, 1992

[54] METHODS AND APPARATUS FOR USING NUCLEAR MAGNETIC RESONANCE TO EVALUATE THE MUSCLE EFFICIENCY AND MAXIMUM POWER OF A SUBJECT DURING LOCOMOTION

[75] Inventor: Britton Chance, Philadelphia, Pa.

[73] Assignee: Performance Predictions, Inc., Philadelphia, Pa.

[21] Appl. No.: 439,799

[22] Filed: Dec. 27, 1989

Related U.S. Application Data

[63] Continuation-in-part of Ser. No. 323,079, Mar. 14, 1989, Pat. No. 4,981,136, which is a continuation of Ser. No. 934,735, Nov. 25, 1986, abandoned.

[51] Int. Cl.$^5$ .............................................. A61B 5/055
[52] U.S. Cl. ..................... 128/653.2; 272/70
[58] Field of Search ............. 128/653 A, 653 SC, 707; 324/307, 309; 272/69, DIG. 5; 119/29

*Primary Examiner*—Ruth S. Smith
*Attorney, Agent, or Firm*—Woodcock Washburn Kurtz Mackiewicz & Norris

[57] ABSTRACT

The muscle efficiency of a subject is evaluated with apparatus comprising a nuclear magnetic resonance (NMR) analytical device which comprises a hollow electromagnet having a bore of sufficient size to receive the subject. Any type of animal can be evaluated, in a preferred embodiment a horse or a human is analyzed. A treadmill within the bore and beneath the subject is utilized to produce locmotion of the subject at different rates of work. The NMR analytical device is used to measure at different rates of work the following ratio within a locomotion-producing muscle mass of the subject:

$Pi/PCr$ where Pi is the concentration within the muscle mass of inorganic phosphate and PCr is the concentration within the muscle mass of phosphocreatine. Methods and apparatus are provided for relating the measured Pi/PCr values to the rates of work then being performed by the subject to provide an efficiency profile for the muscle mass.

19 Claims, 2 Drawing Sheets

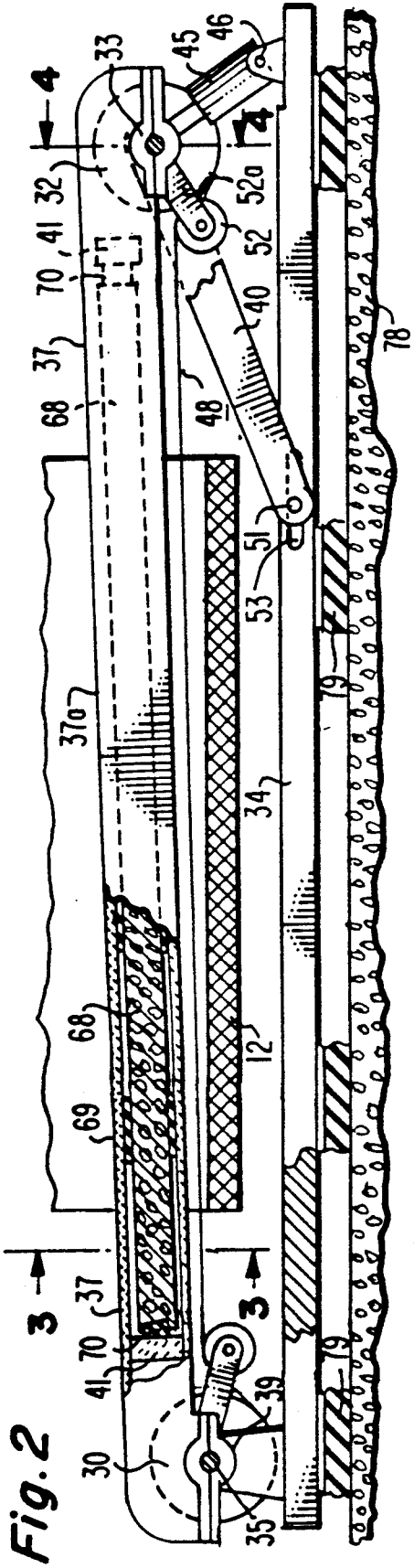

METHODS AND APPARATUS FOR USING NUCLEAR MAGNETIC RESONANCE TO EVALUATE THE MUSCLE EFFICIENCY AND MAXIMUM POWER OF A SUBJECT DURING LOCOMOTION

CROSS REFERENCE TO RELATED PATENTS

This invention is related to U.S. Pat. No. 4,441,502, which issued on Apr. 10, 1984, to Britton Chance, and U.S. Pat. No. 4,452,250, which issued on June 5, 1984, to Britton Chance et al. This is a continuation-in-part of U.S. Pat. No. 4,981,136, issued on Jan. 1, 1991 which is a continuation of U.S. Pat. application Ser. No. 934,735, filed on Nov. 25, 1986 now abandoned.

FIELD OF THE INVENTION

This invention relates to nuclear magnetic resonance (NMR) apparatus for evaluating the muscle efficiency and the maximum power of the muscles of a living animal and, more particularly, relates to apparatus of this type which is capable of performing such evaluation on a large animal, such as a horse or a human, while the animal is engaging in locomotion, especially running, under varying degrees of exercise stress.

The invention also relates to methods of evaluating the performance of such a subject using NMR apparatus for monitoring the muscle biochemistry of the subject while engaged in locomotion under various degrees of exercise stress.

BACKGROUND

One of the above referenced U.S. Pat. No. 4,452,250 Chance et al, is entitled "NMR System for the Non-Invasive Study of Phosphorus Metabolism". This patent provides detailed electrical information relating to the basic construction of NMR apparatus suitable for employment in conjunction with apparatus of the present invention.

The other patent, U.S. Pat. No. 4,441,502 Chance, discloses NMR apparatus for determining the relationship between the work output rate of an exercising human body member and the steady-state capability of oxidative phosphorylation in a muscle responsible for the exercise. In the patent (U.S. Pat. No. 4,441,502), this latter capability is determined by measuring with the NMR apparatus the ratio of the phosphocreatine (PCr) in the muscle to the inorganic phosphate (Pi) at different times during prescribed exercises. This latter ratio is a measure of the muscle efficiency.

Specifically described in this patent, U.S. Pat. No. 4,441,502, is NMR equipment that includes a cylindrical electromagnet and a Cybex ergometer positioned adjacent to the electromagnet and having an oscillatable input lever within the bore of the electromagnet. A human subject places one of his arms within the bore of the electromagnet in a uniform field region thereof and grasps the oscillatable input lever, while the usual transceiver probe coil of the NMR equipment is maintained in proximity to the subject's wrist flexor muscle. The subject them oscillates the input lever by flexing his wrist at prescribed intervals through controlled strokes. Wrist-flexor muscle output is measured by the ergometer while PCr and Pi relationships are measured by the NMR apparatus.

Effective operation of the patented equipment depends upon the subject's carefully following prescribed instructions for the exercises. This being the case, it is difficult to utilize such equipment for evaluating the musculature of non-human animals, particularly untrained animals which can, in fact, include an untrained human. Moreover, the patented equipment permits muscle evaluation only during the performance of relatively simple exercises, such as the above-described repetitive motion of the wrist of the subject, and not during locomotion of the entire subject.

OBJECTS AND SUMMARY OF THE INVENTION

An object of the present invention is to provide, for evaluating the muscle efficiency of a live subject, such as a human or animal, NMR equipment which is not subject to be above described limitations, i.e., it accommodates non-human animals such as horses, even untrained ones, and it allows the horse to perform much more involved exercises while its musculature is being evaluated, such as running under various degrees of exercise stress, even at high speeds simulating those present in competitive events.

The present invention also accommodates humans standing in a fully erect position performing involved exercises, such as running at varying speeds under different levels of exercise stress. Although a human is more capable than a horse of performing this type of exercise in an untrained state, the use of the treadmill controlled by an operator, or other control mechanism, removes the decision making process involving appropriate exercise and stress levels from the subject being tested. Various factors including speed and incline of the belt can be regulated by the controller in response to the NMR readings or other readings This invention may also be used with other types of animals if provisions are made for the animal's size and weight. For the purposes of this invention, whenever the term "animal" is used, this can mean any type of large animal including a horse or a human being. Whenever the term "subject" is used, this also refers to any type of large animal including a horse or a human being. Similarly, in many instances "animals" are referred to but are meant as examples only, and such references and explanations are equally applicable to humans.

Another object is to provide a method of evaluating the performance of an animal by testing the animal during locomotion at varying degrees of exercise stress to derive an efficiency profile for the animal which is of such a character that the profile can be meaningfully compared with similarly-derived efficiency profiles of other animals of similar genetic make-up.

In carrying out the invention in one form, I provide, for evaluating the muscular efficiency of a living animal, apparatus which comprises an NMR analytical device and a tread-mill. The NMR device comprises a hollow electromagnet having a bore in which an axial magnetic field is developed upon energization of the electromagnet. The animal being tested is located within said bore in such a location that a pre-selected muscle mass is located within a region of homogeneous axial field. The NMR device further includes (a) means for interrogating with radio-frequency energy the phosphorus atoms of the biochemicals within said muscle mass while the muscle mass is located within said homogeneous field region and (b) means for developing in response to said interrogation signals representative of the following ratio at the time of the interrogation:

Pi/PCr where Pi is the concentration in said muscle mass of inorganic phosphate and PCr is the concentration in said muscle mass of phosphocreatine. Pi/PCr is also referred to hereinafter as S.

The treadmill comprises a movable belt that extends through the bore in a location that enables said animal to perform work on the movable belt while the muscle mass is in the homogeneous field region The animal runs on the belt, working its muscle mass in the process and causing Pi and PCr to vary in said mass as a function of the level of exercise stress.

This invention is desireable over prior inventions in that it allows the subject to be evaluated while its whole body is in locomotion, thus closely simulating competitive or other situations for which data is required. It allows an untrained animal to be evaluated, especially one that is difficult or impossible to give instructions to.

Means is provided for measuring the rate of work (V) performed by the animal on the treadmill belt during a test of the animal, and additional means is provided for relating Pi/PCr to the rate of work then being performed by the animal, thereby to provide an efficiency profile, or transfer function, for the muscle mass.

By determining Pi/PCr (or S) for a relatively low value of V, which is a relationship that is apparent from the efficiency profile, it is possible to accurately calculate Vm, the maximum work rate of the animal without dangerously stressing the animal. This is done by solving the following equation for Vm, using the above values of V and S:

$$\frac{V}{Vm} = \frac{1}{1 + \frac{Km}{S}}$$

where Km is Michaelis affinity constant (or 0.53). With information available early in the test as to Vm, the test on the animal can be more safely conducted by allowing it to be terminated or otherwise modified when the work rate V approaches Vm.

The rate of work V is sometimes referred to herein as power, and Vm is sometimes referred to herein as the maximum power.

Because the NMR equipment is used for evaluating the concentration of phosphorus compounds in the tissue, it is sometimes referred to herein as phosphorus-NMR equipment or P-NMR equipment. It can also be described as magnetic resonance spectrometer (MRS) equipment.

BRIEF DESCRIPTION OF DRAWINGS

For a better understanding of the invention, reference may be had to the following description taken in conjunction with the accompanying drawings, wherein:

FIG. 2 is a side elevational view of the equipment of FIG. 1 showing certain features in addition to those shown in FIG. 1 and omitting certain others for simplicity.

FIG. 3 is a sectional view along the line 3—3 of FIG. 2.

FIG. 4 is a sectional view along the line 4—4 of FIG. 2.

FIG. 5 is an efficiency profile, or transfer-function, in which rate of work is plotted against biochemical cost for different rates of work. Tests on two different test subjects are illustrated.

FIG. 6 is a graph showing muscle efficiency S/V plotted against S using values of S and V derived from the curves of FIG. 5.

DETAILED DESCRIPTION OF PREFERRED EMBODIMENT

Figure 1:
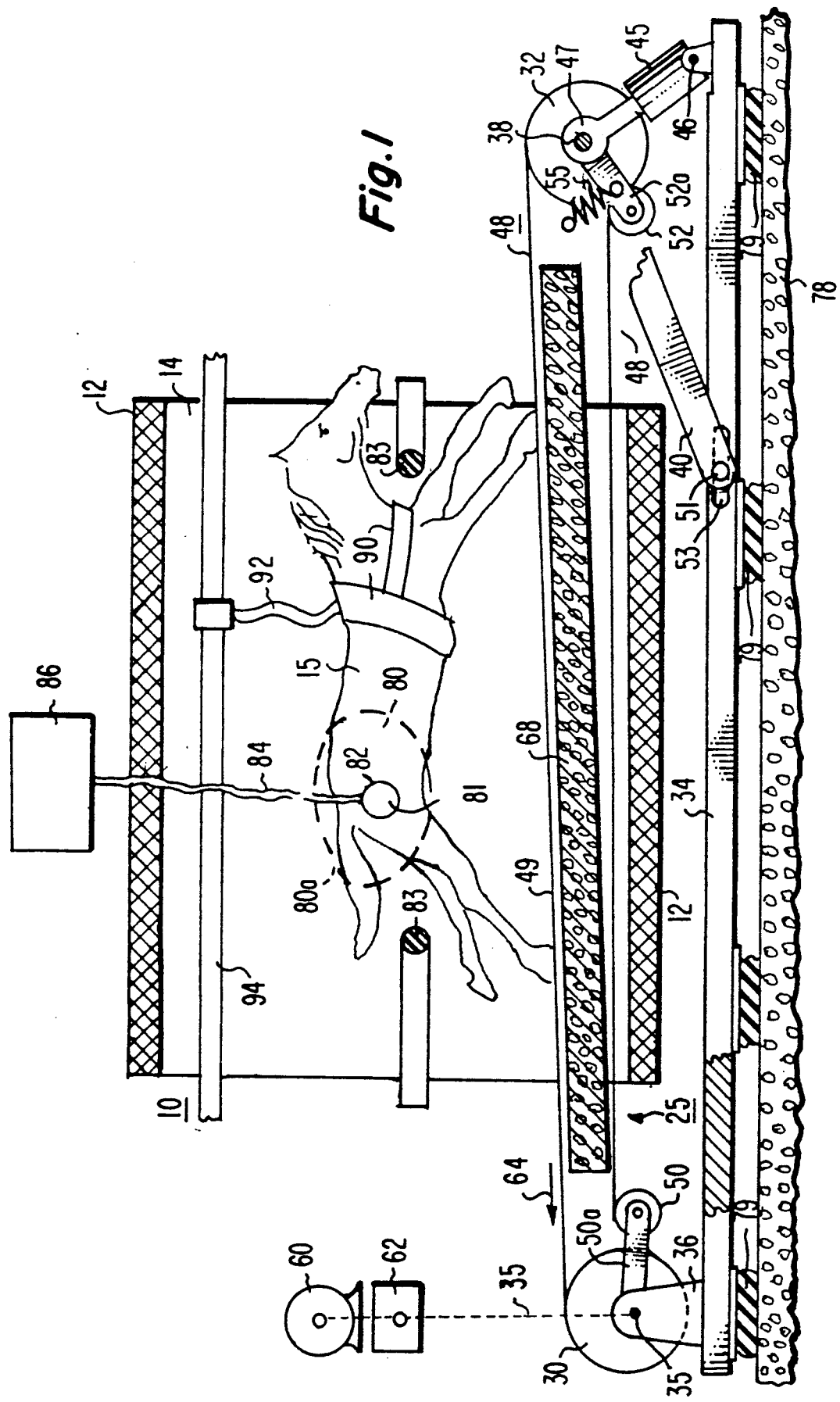
FIG. 1 is a cross-sectional view, partly diagrammatic, showing test equipment embodying one form of the invention being used for evaluating the muscle efficiency of an exercising horse.

Referring now to the FIG. 1, the test equipment shown therein comprises an NMR analytical device 10 that comprises a cylindrical superconducting electromagnet, or coil, 12 having a bore 14 in which an axial magnetic field is developed upon energization of said electromagnet. In one embodiment of the invention, the cylindrical electromagnet 12 has an internal diameter of about 3.5 meters so that a large test subject, such as a horse 15, can readily be accommodated within its bore 14. The length of the illustrated electromagnet is 4.5 meters.

This same embodiment would be appropriate for evaluating other large animals such as humans. It will be understood therefore, that the internal diameter of the electromagnet 12 must be sufficiently large to accommodate whatever type of animal is being evaluated.

THE TREADMILL 25

A treadmill 25 is provided for exercising the horse while it is located within the bore 14 so that major muscles of locomotion in the horse can be evaluated for efficiency. The treadmill comprises a belt 48 which encircles a pair of non-magnetic stainless-steel, dynamically-balanced rollers 30 and 32 which are located outside the coil 12 and spaced from opposite ends of the coil. These rollers are mounted on a horizontally-extending, non-magnetic, stainless steel frame 34 in locations at opposite ends of the frame. Frame 34 is referred to herein-after as a lower frame. In a preferred embodiment, the center lines of the two rollers are spaced apart by approximately 9.5 meters. One of the rollers 30 is used for driving the belt 48. This roller 30 is keyed to a drive shaft 35 that is journalled in bearings in a pair of identical vertically-extending brackets 36 fixed to the lower frame 34. Only one of the brackets 36 is shown in FIG. 1. The other roller 32 is fixed to a rotatable shaft 38 that is journalled at its respective opposite ends in bearings 33 supported on the lower frame 34 in a manner best illustrated in FIG. 2.

Referring to FIG. 2, there is shown an upper frame 37 that extends between the rollers 30 and 32 and is supported at its left-hand end on the drive shaft 35 by suitable bearings 39. This frame 37 comprises two identical beams 37a (only one of which is shown in FIG. 2) located at opposite sides of the belt 48 and joined together by cross-beams 41. At its right-hand end, the upper frame 37 carries the bearings 33 in which the shaft 38 of the roller 32 is journalled. Preferably, the upper frame 37 is made of laminated hardwood.

Referring to FIG. 1, for adjusting the vertical position of right-hand roller 32, two hydraulic rams 45 are provided. These rams 45, only one of which is shown, are located at opposite ends of the shaft 38 and are connected between the shaft 38 and the lower frame 34 by pivotal connections at 46 and 47. These rams are actuated in unison by a suitable motor-driven pump (not shown) to shift the shaft 38 either upwardly or downwardly, as may be desired by the equipment operator. The purpose of such shifting will soon be explained.

The belt 48 that encircles the rollers 30 and 32 of the treadmill is preferably about 1.25 meters in width and is made of rubber, or any other suitable polymer, in a matrix with suitable non-metallic fibers. The belt 48 has upper and lower runs that extend through the bore 14 of the electromagnet. The upper run of the belt 48 provides an upwardly facing surface 49 upon which the horse 15 performs its locomotion exercise, i.e., runs, during testing. The lower run of the belt is directed through the bore of the electromagnet by means of two guide rollers 50 and 52 respectively mounted on levers 50a and 52a, which are respectively pivotally mounted on main shafts 35 and 38. These rollers 50 and 52 bear against the lower surface of the lower run of belt 48 and force the lower run to follow a path closely adjacent the upper run, thus minimizing the space within bore 14 required for the belt.

Each of the tension rollers 50 and 52 is biased in an upward direction against the bottom run of the belt 48 by a suitable spring. The spring for roller 52 is schematically shown as a tension spring at 55. The guide rollers also maintain the belt 48 under tension so that it can readily be driven by the drive roller 30.

The hydraulic rams 45 are used for changing the effective incline of the upper run of belt 48. For example, when it is desired to increase this incline, the ram 45 is activated to elevate the shaft 38 and the roller 32 mounted thereon. Conversely, when it is desired to decrease the incline of the top run of belt 48, the hydraulic rams 45 are actuated to lower the shaft 38 and roller 32. In a preferred embodiment, the belt incline can be varied between zero and 12 percent grade. An uphill grade for the horse is referred to herein as a positive grade.

For increasing the lateral stability of the upper frame 37, two links 40, one at each side of the upper frame, are provided. Each of these links 40 is pivotally connected between the lower frame 34 and the shaft 38 of roller 32. The connection to lower frame 34 is a pivot connection 51 that includes a slot 53 that permits limited sliding of the pivot along the length of frame 34. The connection to shaft 38 is best shown at 59 in FIG. 4 and comprises a circular hole in link 40 in which shaft 38 is rotatable. The links 40 restrain the upper frame 37 against motion in a direction axial of shaft 38. The sliding pivot connection 51 is designed so that no substantial motion of link 40 is allowed axially of shaft 38.

For supplying driving power to the roller 30, a remotely located electric motor, schematically shown at 60, is provided. A variable speed transmission 62 is provided between the motor 60 and the drive shaft 35. The transmission 62 may be of any suitable conventional type, hydraulic or direct, that permits the speed of shaft 35 to be adjusted to any desired value. The roller 30 will normally be driven by the motor in a counterclockwise direction, driving the upper run of the belt to the left as shown by the arrow 64 in FIG. 1. In a preferred form of the invention, the belt speed can be varied from 1.6 to 72 km/hr. The latter speed is based upon actual peak racing speeds of thoroughbred horses. Also, in a preferred form, the motor and transmission are reversible.

For supporting the horse 15 while it is exercising on the belt 48, there is positioned immediately beneath the upper run of the belt 48 a rigid base plate 68 preferably of concrete heavily reinforced with non-magnetic stainless-steel mesh. Alternatively, the base plate 68 may be of a heavy stainless-steel polymer sandwich. In one embodiment, the base plate has on its upper surface a relatively thick coating of thermoset polymer with a low coefficient of friction. This base plate 68 is supported on the upper frame 37 by rubber isolation mounts 69, 70, and 71 (FIGS. 2 and 3) located between the base plate and the upper frame. The isolation mounts 69 are located at spaced points along the top and bottom of the base plate 68, isolation mounts 70 are disposed at the ends of the base plate between the base plate ends and the cross braces 41 of the frame 37, and isolation mounts 71 are located at the sides of the base plate between these sides and the beams 37a. These isolation mounts help to absorb the shocks and vibrations resulting from the horse running on the upper run of the belt 48. The high mass of the base plate also reduces oscillations and high frequency vibrations.

It will be apparent that when the incline of the upper run of the belt 48 is adjusted by actuating the rams 45, the incline of base plate 68 is adjusted by the same amount so that the base plate always lies immediately beneath the upper run and has the same incline as the upper run. This relation-ship is maintained because both the shaft 38 of the roller 32 and the base plate 68 are mounted on the upper frame 37 and move with frame 37 when it is adjusted.

The low-friction material on the upper surface of the base plate 68 allows the belt 48 to move past the base plate without undue frictional opposition despite the weight of the exercising horse on the top run of the belt. To further reduce this frictional opposition, small quantities of suitable fluid lubricant can be continuously fed onto the top surface of the base plate 68. For still further reducing friction between the belt and the base plate, compressed air may be continuously fed through a network (not shown) of angled vents, each of about 2 mm. diameter, distributed throughout the base plate leading to its top surface.

To avoid distortion of and interference with the magnetic fields present within and surrounding the NMR device, it is important that all components of the treadmill be of non-magnetic materials. It is desirable to avoid using for these components metals of any kind, but where this is not feasible, the metal used should be non-magnetic stainless steel. For example, the rollers 30, 32, shafts 35 and 38, rams 45, links 40, guide rollers 50 and 52, and the lower frame 34, are all of non-magnetic stainless steel. It is noted that the lower frame 34 of the treadmill is mounted on a concrete floor 78 by a plurality of vibration-isolating mounts 79, Each of these mounts comprises a synthetic rubber block with a non-magnetic stainless steel cap at its top.

A similar treadmill can be used to evaluate humans or other types of large animals. As will be readily understood by those of ordinary skill, the treadmill for a particular subject may require a different range of speeds based on its expected peak performance speed and lower speeds that might be desirable to measure.

An important parameter that is used in evaluating the horse 15 being tested on the treadmill 25 is the rate of work performed by the horse while exercising on the belt 48, i.e., the power output of the horse. The work performed in a given period of time can be expressed as:

$$Work = M(Dv + Dvg) \qquad \text{(Eq. 1)}$$

where M is the mass of the horse, Dv is the vertical displacement of the horse on the treadmill during the time period, and Dvg is the vertical component of the horse's gait. The vertical displacement Dv is equal to the distance moved by the belt during the given time period multiplied by the percentage incline of- the top run of belt 48. The vertical component of the gait is obtained from a suitable conventional accelerometer attached to the horse. The upward vertical motion recorded by the accelerometer is integrated over the given time period to yield Dvg. Suitable instrumentation is provided for measuring the distance moved by the belt per unit of time and for integrating upward vertical motion signals from the accelerometer.

These components and calculations are also important for the evaluation of other animals including humans.

THE NMR ANALYTICAL DEVICE 10

As stated hereinabove, the NMR device 10 comprises a cylindrical superconducting electromagnet 12 having a bore of about 3.5 meters in diameter for accommodating the entire horse 15 or other animal which is being evaluated. The superconducting electromagnet 12 is energized and maintained by direct current to produce an axial field extending through bore 14. Within the bore 14 there is a region 80 of uniform, or homogeneous, axial magnetic field in the shape of an ellipsoid 80a having a major axis of about one meter in length. It is important that the muscle mass being evaluated by the NMR device be positioned within this homogeneous field region 80 during all measurements taken by the NMR device. This is a necessary condition for accurate measurements.

In the illustrated embodiment, the muscle mass being evaluated is that portion 81 of the horse's gluteus muscle that is aligned with a radio-frequency coil 82 that is taped or otherwise fixed to the horse's skin in alignment with the gluteus muscle. To assure that muscle portion 81 remains within the region 80, adjustable barriers 83 of non-metallic, thermoset polymer material are provided ahead of and behind the horse 15. These barriers 83 constrain the horse within the space between the barriers while the horse is running on the treadmill belt 48. So long as the horse remains in this location and is running on the belt, the region 81 of its gluteus muscle remains within the homogeneous field region 80.

Similarly, the gluteus muscle of the human or other large animal must be within the homogeneous field and aligned with a radio frequency coil that is taped on the skin outside the muscle. Similar restraints should be provided for other large animals including humans. For humans in particular, the restraints may not need to be as rigid since a human can probably pace himself to stay within certain boundaries in the electromagnet; this might not be true for untrained humans. Another alternative for the human subject is to have a non-metallic bar in front of the subject that the subject keeps her hands on while performing the required exercise. As long as the subject's hands stay on the bar, the subject is within the region described above. This is also a useful safety feature as discussed below.

The above-mentioned radio-frequency coil 82 is the conventional transceiver probe coil of the NMR device. In one embodiment of the invention, it is a copper coil of about 10 cm in diameter. Coil 82 is shown connected through conductive leads 84, which are of non-magnetic conductive material, to an electronic control system 86 which corresponds to the control system depicted in block form in FIGS. 4 and 5 of the above-referenced U. S. Pat. No. 4,452,250—Chance et al. As explained in that patent, this electronic control system 86 includes pulse transmitter and receiver circuits designed to study the phosphorus metabolism of the muscle at a frequency corresponding substantially to the nuclear-magnetic-resonance frequency of phosphorus-31. If the static magnetic field developed by the electromagnet is 14 kilogauss, the nuclear-magnetic-resonance frequency of the phosphorus-31 is 24.33 MHz.

The next three paragraphs hereof will briefly summarize the operation of control system 86, making reference to system components and operation described in detail in the aforesaid U.S. Pat. No. 4,452,520—Chance et al. For convenience, the parts of control system 86 will be designated herein with the same reference numerals as used for corresponding parts in the patent, except they will be enclosed herein by parentheses. Particular reference should be had to FIG. 4 of the patent.

The electronic control system includes a computer (22) which acts to start and terminate each sample acquisition period of a series of repetitive sample acquisition periods. Also included in system 86 is: (a) a clock (30) which develops signals of the desired frequency and (b) control logic (23) under the control of the computer, the control logic acting to gate off the receiver circuit (25, 27, 34, 28) and apply a predetermined number of cycles of the clock output to a driver circuit (24). The driver circuit acting through a transmitter/receiver (T/R) switch (26) applies this RF signal to the probe coil 82 (16) to rotate the spin axis of the phosphorus species of interest out of alignment with the static field from electromagnet 12.

Following the transmit portion of the cycle, the T/R switch (26) and the logic (23) allow the receiver portion of the system 86 to become active. The Free Induction Decay (FID) of the chemical species of interest induces a minute signal in the probe coil 82 which is then amplified, detected, and filtered by the receiver portions of the system 86, thus providing an output which is an analog of the composite FID.

The analog data is suitably converted to digital form and acquired by the system computer (22). After a sufficient number of samples are acquired and averaged to improve the signal-to-noise ratio, a Fourier transform is performed to separate the frequency components of the signal. Since the demodulator (28) within the receiver portion uses the above-mentioned clock as a reference, the transformed spectrum is in terms of deviation from the clock frequency, and the areas under the respective peaks in the resulting signal are a measure of the relative concentrations of the various species. Typical forms of this output signal are illustrated in FIGS. 3A and 3B of the above-referenced U. S. Pat. No. 4,441,502.

The above-described signal derived from system 86, when the system is used for evaluating the phosphorus-31 metabolite, has multiple peaks representative of the concentrations of various phosphorus components in the tissue being evaluated. Two of these peaks respectively represent the concentrations of phosphocreatine (PCr) and inorganic phosphate (Pi). The computer in system 86 is designed to provide a digital display of the ratio of the concentrations of Pi and PCr in the muscle at any given time during the test.

The ratio of the concentrations of Pi and PCr (referred to herein as Pi/PCr or S) is a measure of the biochemical "cost" of the work performed by a muscle. As work is performed by the muscle and stress on the muscle increases, the PCr concentration will fall and the Pi concentration will increase, the sum of the two concentrations remaining essentially constant. If a graded series of work performances is executed, each at steady state, and Pi/PCr is recorded for each work performance, a graph such as shown at A in FIG. 5 can be plotted. In this graph, the work rate (or power) V is the ordinate and Pi/PCr (or the biochemical cost) is the abscissa. This graph may be thought of as a "work cost" diagram, or transfer function, or an efficiency profile.

Referring to FIG. 5, the greater the work rate for a given biochemical cost, the greater the biochemical efficiency. For example, in FIG. 5 the solid-line curve A represents the biochemical efficiency of a superior performer, whereas the dotted line curve B represents that of a moderate performer. It will be apparent from these curves that for all biochemical costs except the rest values, the biochemical efficiency of the superior performer exceeds that of the moderate performer.

In testing a horse on the equipment of FIGS. 1-4, the horse, after appropriate warm-up exercises, is walked onto the treadmill and then is exercised by running at a preselected number of work rates, e.g., four. The speed of the belt 48 is increased until the desired work rate V is achieved on a steady-state basis, and then the biochemical cost of this work rate in terms of Pi/PCr is determined. A biochemical efficiency profile of the type shown in FIG. 5 is developed for each test.

This same procedure is appropriate for evaluating any large animal including a human.

The equation for the curve of FIG. 5 can be expressed as:

$$\frac{V}{Vm} = \frac{1}{1 + \frac{Km}{S}} \qquad (Eq.\ 2)$$

where
  S = Pi/PCr, as defined hereinabove,
  Km = Michaelis, affinity constant, which is 0.53,
  V = the work rate of the subject, and
  Vm = the maximum work rate of the subject.

With known values of V and S, Vm can be readily determined from this equation. Thus, by deriving S at a small value of V, Vm can be determined at a work rate that does not dangerously stress the subject With this knowledge as to Vm, the test can be terminated or modified before the subject is dangerously stressed A more detailed discussion of Equation 2 and related aspects of this subject matter is contained in a paper by applicant, B. Chance, and others published in December, 1985 in the Proceedings of the National Academy of Science, Volume 82, pages 8384-8388, which paper is incorporated by reference in the present application.

This equation can be rewritten after simple algebraic manipulation as the following equation:

$$\frac{S}{V} = \frac{1}{Vm}(Km + S) \qquad (Eq.\ 3)$$

which can be plotted as the two curves shown in FIG. 6 from the values derived from the two curves of FIG. 5. Referring to FIG. 6, S/V is the efficiency of the muscle in terms of energy cost per unit of work rate, or power, and 1/Vm is the slope of the particular curve.

From the profile of FIG. 5, it is possible to obtain a good indication of the genetic capability of the subject, its adaptation to training, and its nutritional status. The above-described test can be repeated at appropriate intervals during a training program, and by comparing the efficiency profiles obtained at different times, the effects of training and nutrition can be readily quantified. Thus, this NMR testing equipment can be used to determine which training and nutritional regimes permit optimal expression of a subject's genetic potential for competitive performance or any other type of situation that can be simulated on the treadmill.

To assist in evaluating the subject during its exercising on the treadmill, other biological functions and characteristics are measured through appropriate instrumentation during the test. For example, the subject's core temperature, both rate of change and current actual temperature, is monitored from an electronic thermometer placed in its rectum or other type of temperature measuring device. Its heart rate, both transient and cumulative, is monitored through surface electrodes, thus keeping the treadmill operator informed about the biological stress the subject is undergoing throughout the test. Also the subject's oxygen uptake is suitably measured as the test proceeds in order to determine that such uptake is adequate to meet the needs of the exercising muscle.

Another biochemical measurement that is made during the test is the concentration of lactic acid within the exercising muscle as the maximally exercised state of the muscle is approached. This lactic acid in its ionized form in solution with body fluids is referred to as "lactate" or "muscle lactate." The NMR apparatus can measure the lactate concentration at the various work rates, thus giving the work rate at which the "anaerobic threshhold" (i.e., V→Vm) is reached and also giving a plot of lactate concentration v. work rate. As the anaerobic threshold is approached, the concentration of lactate within the muscle begins to rise suddenly, and this serves as a warning to the operator or to the automatic control that the muscle is entering a dangerous state of fatigue. The operator or the control responds to this condition by discontinuing the test or reducing its severity.

Lactate is an intermediate product of a specific biochemical pathway sometimes called anaerobic glycolysis. Rapidly increasing concentration of lactate within muscle tissue signifies the increased use of this particular pathway in muscle and the increased recruitment of certain muscle-fibre types which favor this form of energy production most heavily. Since the capacity for anaerobic glycolysis is finite and quite limited, the onset of a sudden rise of lactate in the tissues signifies the onset of fatigue. Lactate measurement with this NMR equipment involves interrogating the muscle mass for the hydrogen atom of the methyl group of the lactate. The NMR frequency used for such study is approximately twice that used for the phosphorus metabolism study.

Although provision is made in this apparatus for lactate determination, a significant advantage of this apparatus is that Vm can usually be accurately computed from the data supplied by the apparatus without the need for reliance upon lactate measurement. More specifically, by measuring S, or Pi/PCr at a low value of V, Vm can be derived from Equation (2) hereinabove without the need for dangerously stressing the subject.

It is to be noted that the invention in its broader aspects comprehends measuring with the NMR equipment the concentration of biochemicals other than or in addition to the phosphorus compounds specifically referred to herein, e.g., hydrogen, as pointed out above, and sodium, carbon, potassium, and fluorine.

The efficiency profile of FIG. 5, either alone or taken with the lactate graph referred to immediately above, provides fundamental information on the genetic endowment, genetic expression, and the state of training or nutrition of the animal. This information can be compared with that of other animals, preferably of similar genetic make-up but having different levels of genetic expression, training and/or nutritional status. A data base is accumulated so that performance prediction with respect to a large group of animals is obtained and a particular horse, human, or other large animal may be evaluated with respect to this distribution with accuracy. Suitable measures are taken to ensure the privacy of such information, such as the assigning of secret codes.

A program can be designed to identify untrained horses of high genetic potential and to periodically monitor such horses with the disclosed equipment during training in order to design optimal training regimes and nutritional programs leading to optimal performance. The data acquired will provide the basis not only for early performance prediction and optimizing of genetic potential, but also for warnings of overtraining in the racing animal. A data base is gathered for the NMR evaluated performance or "transfer functions" of all horses of comparable genetics, training, nutrition and age. This data base readily lends itself to the prediction of the performance of a horse in competition with respect to a large group of competitors.

This same program as described in the previous paragraph can be used with other subjects, including humans, whether competitive or not. In addition to the athletes, this invention is useful for humans of different athletic ability levels to determine the possibility of improvement. The invention can also monitor and evaluate different training and nutritional programs while detecting over-training. This would allow an athlete to train to her maximum potential without crossing the line of beneficial exercise into over-exertion. Additionally, the progress of a patient undergoing physical therapy or other rehabilitation can be monitored.

RECOVERY PROTOCOL

Another way in which the apparatus of FIGS. 1-4 may be used is to evaluate the ability of a subject to recover from exercise. Such ability is an indication of the intrinsic genetic capability of the animal, the impact of training and nutritional regimen upon recovery time, or, indeed, the effect of overtraining.

One way of initiating this protocol is to have the animal perform on a track at a prescribed distance and speed appropriate to its training status. Immediately thereafter, the animal is walked into the bore 14 of the electromagnet 12, and the values and changes in phosphocreatine and inorganic phosphate concentrations in the animal's muscle mass are observed not only to determine the intensity of the energy cost measured immediately after completing the performance stress, but also the rate of recovery therefrom. During this period, the animal will be walked leisurely on the treadmill.

This rate of recovery from exercise is in direct proportion to the effectiveness of oxygen and metabolite delivery to the oxidative phosphorylation mechanism and is evaluated by the time course of the recovery to normal of the Pi/PCr ratio; as determined from the increase of the PCr peak of the MRS (or NMR) spectrum and the decrease of the Pi peak. This ratio, when plotted against time, gives the slope that is enzyme capacity, the efficiency of the delivery of nutrients and oxygen to the tissue. Any deficiency of oxidative enzymes in the glycolytic, or citric acid cycles or the mitochondria themselves would be detected.

A subject which has a good endurance potential has little ATP depletion and a rapid recovery. If the horse or performing human athlete is in the sprint category it will have a large depletion of ATP and hence a large proportion of the fibers in the fast twitch category; and if it shows, at the same time, a rapid recovery from stress, it would be judged to have a high genetic expression in favor of a short distance, high speed animal.

It is to be understood that the sprint test can also be accomplished in the magnet with the treadmill tilted. Either procedure is appropriate to prepare the horse, human, or other animal for the above described measurements.

SAFETY FEATURES

To assist in protecting the horse against injury during the above-described tests, the horse is provided with a safety harness 90 of leather and non-magnetic stainless steel. This harness includes heavy leather strapping 92 that loosely connects the horse to a stationary overhead beam 94, preferably of laminated hardwood. An automatic safety switch (not shown) responsive to tension in the strapping 92 is actuated through the strapping should the horse stumble or be unable to maintain pace while performing on the treadmill. This switch controls the operating circuit of treadmill motor 60 and acts to interrupt this circuit and thus stop the motor should the horse stumble or be unable to keep pace with the moving treadmill belt.

Such a harness would also be appropriate for other types of animals including humans. An alternative for the human embodiment is to provide a non-metallic handrail or bar in front or on the sides of the exercising subject so that if the subject stumbles, she can hold herself up with the bar. This bar should be incorporated with some type of safety switch. One example would be to have a strap or cord attached to the subject at one end and to a kill switch, or switch that automatically turns off the treadmill at the other end. If the subject falls or cannot keep up with the treadmill, the strap/cord is pulled by the lagging/falling subject and the treadmill is instantaneously stops. Another example of such a switch would be a kill switch located on the above-mentioned safety bar. The subject would keep her hand on the switch located on the bar; as soon as the subject released the switch, the treadmill would stop instantaneously.

Another safety feature present in the disclosed equipment is a cooling fan for the exercising animal. Such a cooling fan (not shown) is placed a substantial distance from the electromagnet 12 and acts to provide effective body cooling of the horse or other exercising subject. Such cooling is needed to prevent physical collapse and potentially-fatal hyperthermia should the central core temperature exceed a certain level, in the case of the horse should the central core temperature exceed 42° C.

for some time, as it may in severe exercise, the animal would be at risk. The fan most preferably has a variable-speed drive motor which is suitably controlled to operate at a speed which is a function of the treadmill speed.

CONTROL OF THE TREADMILL

The following are the major control functions for the treadmill: start, stop, speed control, inclination, timer and emergency stop. In a preferred form of the invention, an automatic control (not shown) is provided for the treadmill equipment that includes a suitable microcomputer that is programmable to implement these control functions, with manual override and reset available at all times. This programmability provides an infinite variety of protocols and permits standard procedures to be easily set. For example, any of the following protocols may be set: step-wise progression or ramp function for speed or inclination of the belt, or combinations of these. Reliable biological data such as heart-rate and body-core temperature may be used in a feedback loop to the controlling computer to vary the workload or activate the emergency stop.

As a supplement to the above automatic control, the equipment will be under the control of a human operator (not shown). This operator is seated adjacent but outside the electromagnet 12 in a position where he can clearly view displays of the various measured parameters and the animal within the bore 14 during the test. These parameters include the elapsed time of the complete test and of selected portions of the test, the work rate of the subject, the incline or grade of the treadmill belt, the heart rate and temperature of the subject, and the Pi/PCr ratio of the muscle being evaluated. In a typical operator-controlled test, the operator runs the treadmill at a speed that produces a predetermined work rate by the subject He maintains this work rate for a prescribed period and then increases this work rate to a new level for another prescribed period, thereafter repeating this step two additional times. At each work level, the equipment obtains a value of Pi/PCr and at the end of the test the equipment plots Pi/PCr for the different work levels to provide the desired transfer function or efficiency profile. If the control is by the operator alone, he carefully monitors the subject's heart rate and temperature during the test and would terminate the test if either of these rises to an unsafe level.

Although the preferred form of treadmill used in practicing the invention is one which is driven by a suitable motor, as illustrated in FIG. 1, it is to be understood that the invention in its broader aspects can be practiced by using the type of treadmill that is driven instead by the exercising animal. In this latter type of treadmill, an absorption dynamometer including an adjustable friction brake is coupled to the shaft of one of the rollers for imposing a load on the roller and belt and, hence, the exercising subject, and for providing a measure of the work rate of the subject.

With either type of treadmill, while the test is under way, an attendant (not shown) may stand beside the horse or other animal if necessary on a stationary platform located inside the bore 14. The horse can be provided with the usual bit that is held in its mouth and a bridle coupled to the bit. The bridle includes reins that may be held by the attendant during the test. With the type of treadmill illustrated, the attendant is required to exercise much less control over the horse than with a horse-driven treadmill. With the illustrated treadmill, primary control over the horse is exercised through the treadmill rather than by "conditioned-reflex" control of the horse by an attendant.

For other animals, similar control is required if the animal is to drive the treadmill In the case of a human being evaluated on a human-driven treadmill, the control exerted by the attendant can be through oral commands or visual signals, thus, possibly not requiring the attendant to be located within the electromagnet.

Although particular applications for the disclosed apparatus have been described, many other applications falling within the spirit of this invention Will be apparent to those skilled in the art. Also it will be obvious that various changes and modifications may be made in the apparatus shown without departing from the invention in its broader aspects. It is, therefore, intended in the appended claims to cover all such changes and modifications as fall within the true spirit and scope of the invention.

What we claim as new is:

1. Apparatus for evaluating the muscular efficiency of a living animal during locomotion comprising:
   (a) an NMR analytical device comprising: (i) a hollow electromagnet having a bore in which an axial magnetic field is developed upon energization of said electromagnetic, the bore being of sufficient size to receive said animal, (ii) means for locating said animal within said bore in such a location that during said locomotion a preselected locomotion-producing muscle mass of the animal is located within a region of homogeneous axial magnetic field, (iii) means for interrogating with radio frequency energy pulses the phosphorus atoms of the biochemicals within said muscle mass while the muscle mass is located within said region of homogeneous axial magnetic field, and (iv) means for developing, in response to said interrogation, signals representative of the following ratio of phosphorus-containing components within said muscle mass at the time of the interrogation:

Pi/PCr where Pi is the concentration in said mass of muscle inorganic phosphate and PCr is the concentration in said mass of muscle phosphocreatine,
   (b) a treadmill comprising a movable belt that extends through said bore in a location that enables said animal to perform locomotion on said movable belt while said muscle mass remains in said region of homogeneous axial magnetic field, said locomotion exercising said muscle mass and causing Pi and PCr to vary in said muscle mass as a function of the level of exercise stress,
   (c) means for measuring the rates of work performed by said animal on said treadmill belt during locomotion of the animal,
   (d) means for relating the values of Pi/PCr measured during locomotion to the rates of work then being performed by said animal to provide an efficiency profile for said muscle mass, and
   (e) means for evaluating the ability of said muscle mass to recover from said exercise, comprising means for recording or observing the return toward normal at-rest values of at least one of Pi and PCr or a quantity based upon at least one of Pi and PCr.

2. A method of evaluating the performance ability of animals, comprising:

(a) using apparatus as defined in claim 1 for developing efficiency profiles for individual animals in a group of animals having similar genetic make-up, and evaluating the ability of said individual animals to recover from exercise, (b) storing such efficiency profiles and abilities to recover in a data base, (c) using apparatus as defined in claim 1 for developing an efficiency profile for another individual animal having a genetic make-up similar to those of the animals in said group, and evaluating the ability of said other animal to recover from strenuous exercise, and (d) comparing at least one of (i) the efficiency profile of said other animal with those stored in said data base and (ii) the ability to recover of said other animal with those abilities stored in the data base.

3. A method as defined in claim 2 in which:

(a) efficiency profiles are selected from said data base for animals of similar age that have had similar training and nutritional experience, (b) the individual animal of (c), claim 6 is similar in age, training and nutritional experience to the animals whose efficiency profiles are selected, and (c) comparing the efficiency profile of said other animal to those selected from said data base, thereby providing data for predicting the performance of said other animal in competition with competitors.

4. Apparatus for evaluating the muscular performance of a living animal during locomotion by the animal, comprising:

(a) an NMR analytical device comprising: (i) a hollow electromagnet having a bore in which an axial magnetic field is developed upon energization of said electromagnetic, the bore being of sufficient size to receive said animal, (ii) means for locating said animal within said bore in such a location that during said locomotion a preselected locomotion producing muscle mass of the animal is located within a region of homogeneous axial magnetic field, (iii) means for interrogating with radio-frequency energy pulses predetermined atoms of the biochemicals within said muscle mass while the muscle mass is located within said region of homogeneous axial magnetic field, and (iv) means for developing, in response to said interrogation, signals representative of a measured biochemical relationship within said muscle mass at the time of interrogation, (b) means for causing locomotion of the animal while in said bore at varying rates of work that cause said biochemical relationship to vary within said muscle mass as a function of the level of exercise stress to which the animal is subjected, (c) means for measuring the rate of work performed by said animal while engaged in locomotion within said bore during a test of the animal, (d) means for relating the measured biochemical relationship in said muscle mass to the rates of work then being performed by said animal to provide an efficiency profile for said muscle mass, and (e) means for evaluating the ability of said muscle mass to recover from said exercise, comprising means for recording or observing the return toward a normal at-rest value of said biochemical relationship or a quantity based upon at least said biochemical relationship.

5. The apparatus of claim 4 in which the means for causing locomotion of the animal comprises a treadmill including a movable belt that extends through said bore in a location that enables the animal to perform work on said movable belt while said muscle mass is in said region of homogeneous axial magnetic field, said work exercising said muscle mass and causing said biochemical relationship to vary in said muscle mass as a function of the level of exercise stress.

6. The apparatus of claim 2 in which:

(a) the atoms interrogated with said radio-frequency pulses are phosphorus atoms, and (b) the signals developed in response to said interrogation are representative of the following biochemical relationship within said muscle mass at the time of the interrogation:

$$Pi/PCr$$

where Pi is the concentration in said muscle mass of inorganic phosphate and PCr is the concentration in said muscle mass of phosphocreatine.

7. A method of evaluating the performance ability and ability to recover from exercise of animals, comprising:

(a) using apparatus as defined in claim 4 for developing efficiency profiles for individual animals in a group of animals having similar genetic make-up, and evaluating the ability of said individual animals to recover from exercise, (b) storing such efficiency profiles and abilities to recover in a data base, (c) using apparatus as defined in claim 2 for developing an efficiency profile for another individual animal having a genetic make-up similar to those of the animals in said group, and evaluating the ability of said other animal to recover from strenuous exercise, and (d) comparing at least one of (i) the efficiency profile of said other animal with those stored in said data base and (ii) the ability to recover of said other animal with those abilities stored in the data base.

8. A method as defined in claim 7 in which:

(a) efficiency profiles are selected from said data base for animals of similar age that have had similar training and nutritional experience, (b) the individual animal of (c), claim 7 is similar to age, training and nutritional experience to the animals whose efficiency profiles are selected, and (c) comparing the efficiency profile of said other animal to those selected from said data base, thereby providing data for predicting the performance of said other animal in competition with competitors.

9. A method of evaluating the performance ability and ability to recover from exercise of horses comprising:

(a) subjecting individual horses in a group of horses having similar genetic make-up to tests in which there is obtained for each of the individual horses an efficiency profile and ability to recover from exercise, the test for each horse comprising placing said horse in the bore of the electromagnet of an NMR analytical device, exercising the horse by utilizing a treadmill beneath the horse to produce locomotion of the horse at different rates of work while is said bore, measuring during said locomotion the rate of work performed by the horse and concurrently measuring with the NMR analytical device the following ratio of phosphorus-containing components within a locomotion producing muscle mass of the horse: Pi/PCr, where Pi is the concentration in said muscle mass of inorganic phosphate and PCr is the concentration in said muscle mass of phosphocreatine, the efficiency profile being a representation of work rate versus Pi/PCr for different levels of exercise stress, and determining said ability to recover by at least observing the return toward normal at-rest values of Pi/PCr or a quantity based upon Pi/PCr, (b) storing said efficiency profiles and abilities to recover in a data base, (c) developing an efficiency profile for another individual horse having a genetic make-up similar to those of the horses in said group, and evaluating the ability of said other horse to recover from strenuous exercise, by subjecting said other individual horse to the same test and measurements as defined in paragraph (a), and (d) comparing at least one of (i) the efficiency profile of said other horse with those stored in said data base and (ii) the ability to recover of said other horse with those abilities stored in the data base.

10. A method as defined in claim 9 in which:

(a) efficiency profiles are selected from said data base for animals of similar age that have had similar training and nutritional experience, (b) the other horse of (c), claim 9 is similar in age, training, and nutritional experience to the horses whose efficiency profiles have been selected, and (c) comparing the efficiency profile of the other horse to those selected from said data base, thereby providing data for predicting the performance of the other horse in competition with competitors.

11. A method for evaluating the muscle efficiency and ability to recover from exercise of a subject during locomotion, comprising:

(a) placing the subject within the bore of the electromagnet of an NMR analytical device, (b) exercising said subject by utilizing a treadmill beneath the subject to produce locomotion of the subject at different rates of work while in said bore and measuring with the NMR analytical device at different rates of work the following ratio of phosphorus-containing components within a locomotion-producing muscle mass of the subject:

Pi/PCr where Pi is the concentration in said muscle mass of inorganic phosphate and PCr is the concentration in said muscle mass of phosphocreatine, (c) relating said values of Pi/PCr measured during locomotion to the rates of work then being performed by said subject to provide an efficiency profile for said muscle mass, and (d) recording or observing the return toward normal at-rest vales of at least one of Pi and PCr or a quantity based upon at least one of Pi and PCr.

12. The method of claim 11 in which:

(a) the lactate concentration in said muscle mass is measured by said analytical NMR device during said locomotion exercising, and (b) the severity of said exercising is reduced when said lactate concentration shows a sudden rise.

13. The method of claim 11 in which:

(a) Vm, the maximum work rate of the subject, is determined by use of test results obtained from the test procedures defined in claim 11 before the anaerobic threshold is reached, and (b) said determination of Vm being effected by applying to the following relationship values of S and V derived from said test procedure:

$$\frac{V}{Vm} = \frac{1}{1 + \frac{Km}{S}}$$

where S is the value of Pi/PCr established at a given work rate V, of the subject, and Km is Michaelis' affinity constant.

14. The method of claim 13 in which the severity of said exercising is reduced before the work rate of the subject approaches a value Vm determined from the relationship defined in claim 13.

15. A method of evaluating the maximum work rate Vm and ability to recover from exercise of a subject without dangerously stressing the subject comprising:

(a) placing the subject on a treadmill located within the bore of an electromagnet of an NMR analytical device, (b) causing the subject to engage in locomotion on the treadmill, thereby causing the following biochemical relationship within a major muscle mass relied upon by the subject for locomotion to vary as a function of the subject's work rate V on the treadmill:

Pi/PCr where Pi is the concentration in said muscle mass of inorganic phosphate, and PCr is the concentration in said muscle mass of phosphocreatine, (c) measuring with the NMR analytical device while the subject is engaging in locomotion on the treadmill: Pi/PCr for a work rate V that does not dangerously stress the subject, (d) determining the maximum work rate Vm from the following relationship:

$$\frac{V}{Vm} = \frac{1}{1 + \frac{Km}{S}}$$

where Km is Michaelis' affinity constant, and S is representative of Pi/PCr measured for said work rate V, and (d) recording or observing the return toward normal at-rest values of at least one of P and PCr or a quantity based upon at least one of Pi and PCr, whereby said ability to recover is indicated.

16. A method for evaluating the ability of a subject to recover from strenuous exercise, comprising:

(a) subjecting the subject to strenuous exercise;

(b) measuring, with an NMR device, at least one of the biochemical relationships present within a muscle mass of the subject following said strenuous exercise; and (c) recording or observing the return toward normal at-rest values of at least one of the measured relationships or at quantity based upon at least one of the measured relationships while the subject continues to exercise at a leisurely pace.

17. A method of evaluating the exercise performance ability and ability to recover from exercise of humans comprising:
- (a) subjecting individual humans in a group of humans having similar genetic make-up to tests in which there is obtained for each of the individual humans an efficiency profile and an indication of the human's ability to recover from exercise, the test for each human comprising placing said human in the bore of the electromagnet of an NMR analytical device, exercising the human by utilizing a treadmill beneath the human to produce locomotion of the human at different rates of work while in said bore, measuring during said locomotion the rate of work performed by the human and concurrently measuring with the NMR analytical device the following ratio of phosphorus-containing components within a locomotion-producing muscle mass of the human: Pi/PCr, where Pi is the concentration in said muscle mass of inorganic phosphate and PCr is the concentration in said muscle mass of phosphocreatine, the efficiency profile being a representation of work rate versus Pi/PCr for different levels of exercise stress, and recording or observing the return, toward normal at-rest values, of at least one of Pi and PCr or a quantity based upon at least one of Pi and PCr,
- (b) storing said efficiency profiles and indications of ability to recover in a data base,
- (c) developing an efficiency profile and information related to the ability to recover from exercise for another individual human having a genetic make-up similar to those of the humans in said group by subjecting said other individual human to the same test and measurements as defined in paragraph (a), and
- (d) comparing the efficiency profile and ability to recover from exercise of said other human with those stored in said data base.

18. A method as defined in claim 17 in which:
- (a) efficiency profiles are selected from said data base for subjects of similar age that have had similar training and nutritional experience,
- (b) the other human of (c), claim 17 is similar in age, training, and nutritional experience to the humans whose efficiency profiles have been selected, and
- (c) comparing the efficiency profile of the other human to those selected from said data base, thereby providing data for predicting the performance of the other human in competition with competitors.

19. A method as defined in claim 17 in which:
- (a) efficiency profiles are selected from said data base for subjects of similar age that have had similar training and nutritional experience,
- (b) the other human of (c), claim 17 is similar in age, training, and nutritional experience to the humans whose efficiency profiles have been selected, and
- (c) comparing the efficiency profile of the other human to those selected from said data base, thereby providing data for predicting the ability and/or potential of the other human to perform this type of exercise.

* * * * *

UNITED STATES PATENT AND TRADEMARK OFFICE
CERTIFICATE OF CORRECTION

PATENT NO. : 5,081,991
DATED : January 21, 1992
INVENTOR(S) : Britton Chance

It is certified that error appears in the above-identified patent and that said Letters Patent is hereby corrected as shown below:

Column 3, line 10, after "region" insert --.--.

Column 9, line 50, after "subject" insert --.--.

Column 9, line 53, after "stressed" insert --.--.

Column 14, line 11, delete "Will" and insert --will-- therefor.

Column 14, line 25, delete "electromagnetic" and insert --electromagnet-- therefor.

Column 15, line 36, delete "electromagnetic" and insert --electromagnet-- therefor.

Signed and Sealed this

Twenty-ninth Day of June, 1993

Attest:

MICHAEL K. KIRK

*Attesting Officer*   Acting Commissioner of Patents and Trademarks